United States Patent [19]

Mestas et al.

[11] Patent Number: 5,085,206
[45] Date of Patent: Feb. 4, 1992

[54] SYSTEM FOR INITIALIZING POSITIONS OF TARGET LOCATING ARM AND DEVICE FOR FIRING FOCUSED SHOTS

[75] Inventors: Jean-Louis Mestas, Chassieu; Bernard Lacruche, Lyons; Dominique Cathignol, Genas, all of France

[73] Assignees: Technomed International; INSERM, both of Paris, France

[21] Appl. No.: 595,679

[22] Filed: Oct. 9, 1990

Related U.S. Application Data

[63] Continuation of Ser. No. 139,437, Dec. 30, 1987, abandoned.

[30] Foreign Application Priority Data

Dec. 31, 1986 [FR] France ................... 86 18441

[51] Int. Cl.⁵ .................... A61B 8/08; A61B 17/22
[52] U.S. Cl. .................... 128/24 EL; 128/660.03
[58] Field of Search ............ 606/1, 128; 128/24 AA, 128/24 EL, 660.01, 804, 660.03

[56] References Cited

U.S. PATENT DOCUMENTS

| | | | |
|---|---|---|---|
| 2,559,227 | 7/1951 | Rieber | 128/24 A |
| 4,185,502 | 1/1980 | Frank | 128/660.01 |
| 4,196,630 | 4/1980 | Rudolph | 128/660.01 |
| 4,291,578 | 9/1981 | Hetz et al. | 128/660.01 |
| 4,341,222 | 7/1982 | Gardineer et al. | 128/660.01 |
| 4,669,483 | 6/1987 | Hepp et al. | 128/660.03 |
| 4,696,299 | 9/1987 | Shene et al. | 128/660.03 |
| 4,705,026 | 11/1987 | Chaussy et al. | 128/328 |
| 4,763,652 | 8/1988 | Brisson | 128/328 |
| 4,796,613 | 1/1989 | Heumann et al. | 128/328 |

*Primary Examiner*—Edgar S. Burr
*Assistant Examiner*—Stephen R. Funk
*Attorney, Agent, or Firm*—Schechter, Brucker & Pavane

[57] ABSTRACT

A method and apparatus for coordinating the initial positions in three dimensions of a device (10) for triggering and focusing shots and a locating arm (14). The apparatus includes structure (20) for calibrating the distance (D) between the free end (14a) of the locating arm (14) and the device (10) for triggering and focusing shots, the calibration structure (20) preferably comprising a link member (22). The invention improves the accuracy with which a target is located and, therefore, the effectiveness with which it is destroyed.

15 Claims, 1 Drawing Sheet

SYSTEM FOR INITIALIZING POSITIONS OF TARGET LOCATING ARM AND DEVICE FOR FIRING FOCUSED SHOTS

This is a continuation of U.S. application Ser. No. 07/139,437 filed Dec. 30, 1987 now abandoned.

The invention relates essentially to a method and apparatus for coordinating the initial positions in three dimensions of a device for triggering and focusing shots on a target point and an arm for locating the position of the target to be shot at.

BACKGROUND OF THE INVENTION

U.S. Pat. No. 2,559,227 (Rieber) describes a device for triggering and focusing shots on a target point which is intended to coincide with a target to be destroyed, for example tissue in a living being, said device being also applicable to destroying lithiases. The device may comprise a truncated elliptical reflector 80 in which shock waves are generated by an electric arc or discharge between two electrodes 12 and 13 which are disposed to coincide at the internal focus of the elliptical reflector which is filled with a liquid 83 for transmitting shock waves, e.g. oil (see FIG. 3 and column 7 line 51 to column 9 line 30).

Similarly, French published patent specification number 2 240 795 describes a similar apparatus in which the liquid is constituted by water (page 3, lines 23 to 24).

French published patent specification number 2 502 485 describes a target-locating arm 18, 20 supporting an ultrasonic target-locating probe 10 at its free end. The locating arm includes six joints, each of which is provided with an angle of rotation detector 26, 28, 30, 32, 34, or 36 in order to establish a diagnosis by displaying a tomogram of the examined sample.

European published patent specification EP-O 169 311 describes a locating arm having a locating probe at its free end which is responsive to X-rays or to ultrasound, and which is mounted on an apparatus for triggering and focusing shots on a target point which is intended to be brought into coincidence with a target to be destroyed, for example a lithiasis. This device for triggering and focusing shots is constituted by a truncated elliptical reflector, with the shots being constituted by shock waves generated in the first focus of the elliptical reflector which focuses these shots on the second focus as described by Rieber in U.S. Pat. 2 559 227.

Thus, the difficulty resides in making the target located by the locating probe situated at the end of the locating arm coincide with the elliptical reflector's second focus which constitutes the target point, with said elliptical reflector being mounted on a support which is displaceable in three mutually perpendicular directions X, Y, and Z. The present inventors have discovered that it is necessary to know the initial or "reference" position in three dimensions of the device for triggering and focusing shots, e.g. an elliptical reflector, and to coordinate said initial "reference" position with the initial "reference" position of the locating arm.

European patent specification number 0 169 311 neither describes nor suggests any such approach.

Thus, an aim of the present invention is to solve a new technical problem consisting in providing a solution capable of coordinating the initial or "reference" position in three dimensions of a device for triggering and focusing shots on a target point which is to be brought into coincidence with a target to be destroyed, e.g. a lithiasis, with the initial or "reference" position of an arm for locating the position of said target, thereby considerably increasing the accuracy of target location and bringing the target located by the locating probe at the end of the locating arm into coincidence with the target point as determined by the device for triggering and focusing shots and thus, unexpectedly, increasing the effectiveness of target destruction.

Another main aim of the invention is to solve the technical problem consisting in providing a solution for coordinating the initial "reference" positions in three dimensions of the device for triggering and focusing shots on a target point which is to be brought into coincidence with a target to be destroyed, e.g. a lithiasis, and a locating arm for locating the position of said target, said arm having a locating probe mounted at the free end thereof, and making it possible to detect imperfections in the three dimensional displacement of said device for triggering and focusing shots and of the locating arm thus making it possible to correct such imperfections, thereby improving, in unexpected manner, the accuracy of target location in three dimensions and the subsequent bringing into coincidence of the target to be destroyed with the target point, thus also giving rise to a concomitant improvement in the effectiveness of target destruction.

These new problems are solved for the first time by the present invention by providing a solution of negligible cost while increasing the number of targets that can be destroyed, e.g. tissues, lithiasis concentrations such as kidney stones or bile stones, etc., and reducing the duration of such shot treatment, by increasing the accuracy with which the target is located and the accuracy with which the target is brought into coincidence with the target point.

SUMMARY OF THE INVENTION

Thus, in a first aspect, the present invention provides a method of coordinating the initial "reference" position in three dimensions of a device for triggering and focusing shots on a target point which is to be brought into coincidence with a target to be destroyed (e.g. a lithiasis), with the initial "reference" position of a locating arm for locating the position of said target, said arm having a locating probe mounted on its free end (e.g. an ultrasonic type probe) in order to enable the target to be brought into coincidence with the target point, the method comprising calibrating the distance between the free end of the arm and the device for triggering and focusing shots.

Preferably, the distance calibrated is the distance between the free end of the arm and the target point.

Advantageously, the calibration is performed by incorporating a link member between the device for triggering and focusing shots and the free end of the arm.

Advantageously, the above-mentioned link member comprises a first link element and a second link element which are hinged to each other about a hinge which advantageously allows for displacement in any of three dimensions, said hinge being preferably of the ball-and-socket type, with the first link element being mounted on the device for triggering and focusing shots and with the second link element being mounted on the free end of the locating arm instead of and in the position of its locating probe.

Preferably each link element is adjustable in length, thereby making it possible in accordance with the invention to bring the hinge point or axis between the link elements into coincidence with the target point by adjusting the length of the link element which is mounted on the device for triggering and focusing shots; with the distance between the free end of the arm and the target point being subsequently adjusted to a reference distance value by acting on the length of the link element mounted on the arm.

Advantageously, this reference distance is not less than the greatest detection depth of the locating probe mounted on the arm.

The device for firing and concentrating shots may be moved successively along three axes X, Y, and Z through predetermined distances in order to detect imperfections in the displacements in three dimensions of the locating arm and/or of the device for triggering and focusing shots.

In a second aspect, the present invention also provides a device for coordinating the initial "reference" position in three dimensions of a device for triggering and focusing shots on a target point which is to be brought into coincidence with a target to be destroyed (e.g. a lithiasis) with the initial "reference" position of a locating arm for locating the position of said target, said arm supporting a locating probe on its free end (e.g. a probe of the ultrasonic type) in order to make it possible to bring the target into coincidence with the target point, the device comprising calibration means for calibrating the distance between the free end of said arm and the device for triggering and focusing shots.

Preferably, said calibration means are means for providing calibration between the free end of the arm and the target point.

Preferably, the above-mentioned calibration means comprise a link member between the device for triggering and focusing shots and the free end of the arm.

This link member may be as defined above.

Advantageously, the device for triggering and focusing shots is constituted by a truncated elliptical reflector of the type described in U.S. Pat. No. 2,559,227 (Rieber) or in French patent specification number 2 247 195.

It will thus be understood that the invention makes it possible to coordinate the initial "reference" position in three dimensions of the device for triggering and focusing shots with the locating arm in a manner which is extremely simple and practical, thereby improving the accuracy with which the target is located and thus the accuracy with which the target to be destroyed is brought into coincidence with the target point as located by the locating probe disposed at the free end of the locating arm. Thus, a significant improvement is achieved in the effectiveness with which targets are destroyed, thereby reducing the number of shots and the duration of treatment, and thus making it possible, in practice, to increase the number of patients that are treated.

BRIEF DESCRIPTION OF THE DRAWINGS

A preferred embodiment of the invention is described below by way of example and with reference to the accompanying drawings, in which.

DESCRIPTION OF PREFERRED EMBODIMENT

Figure 1:
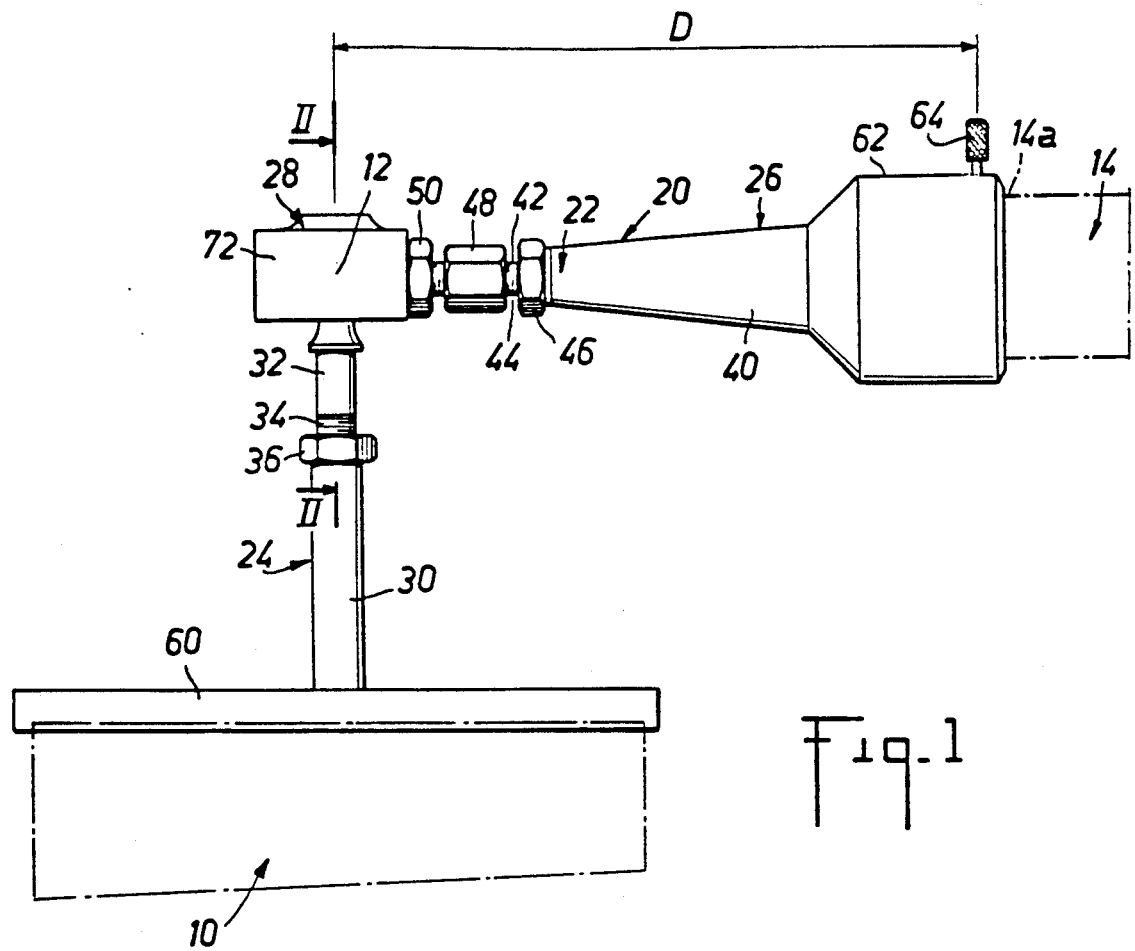
FIG. 1 is a fragmentary elevational view of the presently preferred embodiment of a coordination device in accordance with the invention, the device being shown in position between the locating arm and the device for triggering and focusing shots which is constituted in the present case by a truncated elliptical reflector.
Figure 2:
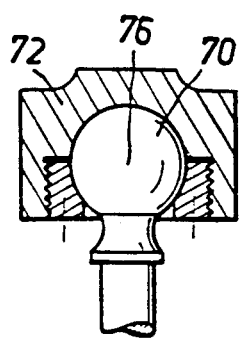
FIG. 2 is a sectional view on line II—II of FIG. 1.

FIGS. 1 and 2 show a device in accordance with the invention for coordinating the initial "reference" position in three dimensions of a device for triggering and focusing shots (represented by a general reference numeral 10) on a target point 12 which is intended to be brought into coincidence with a target to be destroyed, e.g. a lithiasis, with the initial "reference" position of a locating arm given an overall reference 14 and supporting a locating probe e.g. of the ultrasonic type at its free end for the purpose of bringing the target into coincidence with the target point 12. The invention provides calibration means represented by general reference numeral 20 for calibrating the distance D between the free end 14a of the arm 14 and the device 10 for triggering and focusing shots.

Preferably, these calibration means 20 are means for calibrating the distance between the free end 14a of the arm 14 and the target point 12.

In the presently preferred embodiment of the invention, these calibration means 20 comprise a link member given a general reference numeral 22 for providing a link, in this case a mechanical link, between the device 10 for triggering and focusing shots and the free end 14a of the locating arm 14.

In the embodiment shown, this link member 22 advantageously comprises a first link element 24 and a second link element 26 which are hinged to each other by a hinge 28 which is preferably of the ball-and-socket type allowing displacement in all three dimensions, as shown. Thus, one of the link elements, e.g. the first link element, is mounted on the device 10 for triggering and focusing shots, while the other link element, in this case the second link element 26, is mounted on the free end 14a of the locating arm 14 at the location of and in the place of the locating probe.

Each link element 24 and 26 is preferably adjustable in length by being made telescopic. Thus, the first link element 24 comprises a fixed portion 30 having a moving telescopic portion 32 movably mounted therein with displacement thereof being adjustable at will, for example by means of a system comprising a screw 34 and a nut 36.

Similarly, the second link element 26 comprises a fixed portion 40 and a telescopic portion 42 which is displaceable at least in part beyond the fixed portion by means of a conventional telescopic system, e.g. comprising a screw 44 and a nut 46. A plurality of nuts 46, 48, and 50 may be provided so as to increase the accuracy of adjustment. A similar multi-nut system could also be provided on the first link element 24.

It will readily be understood that the first link element 24 which is intended to be mounted, in this case, on the device for triggering and focusing shots is fitted with appropriate means for connecting it thereto. In this case, given that the device for triggering and focusing shots is constituted, for example, by a truncated elliptical reflector, the fixed portion 30 of the first link element 24 is provided with a plate 60 which is fitted over the truncated portion of the elliptical reflector 10. Similarly, the fixed portion 40 of the second link element 26 includes adaptor means 62 for fitting over the free end 14a of the arm 14 and suitable for clamping thereto by means of a clamping element 64 such as a screw.

Further, the hinge 28 which allows for displacement in all three dimensions is preferably of the ball-and-socket type as can be clearly seen in FIG. 2. Thus, the telescopic displaceable portion 32 of the first element 24 terminates with a portion in the form of a hemispherical ball 70 over which the second portion of the hinge constituted by a corresponding and likewise hemispherical cap 72 is disposed, with said second portion being fixed to the displaceable or telescopic portion 42 of the second link element 26. It can thus be seen that the coordination device makes it possible to perform the coordination method described above, as follows:

Initially, the plate 60 is put into position on the device 10 for triggering and focusing shots, in this case a truncated elliptical reflector, and then the portion 62 of the second link element 26 is fitted onto the free end 14a of the locating arm 14.

It will be understood that the device 10 for triggering and focusing shots is mounted on a support which is displaceable in all three dimensions enabling the said device to be moved into any position in three dimensions, with said support being described, for example, in U.S. patent application Ser. No. 07/273,611 now U.S. Pat. No. 4,915,094. The same is true of the locating arm whose free end 14a may be displaced into any position in three dimensions, and may be designed, in particular, to have six numbers of freedom provided by six hinges as described, for example, in French patent specification number 2 502 485 or U.S. patent application Ser. No. 07/117,434.

Thus, in order to coordinate the initial positions, it will be understood that the device for triggering and focusing shots is initially put into an initial position in which the device for triggering and focusing shots is substantially in the vicinity of, or is actually at, its zero position along an X axis, a Y axis, and a Z axis. In this initial position, the length of the first link element 24 of the link member 22 is then adjusted by acting on the adjustment nut 36 so as to bring the axis or hinge point of the hinge 28 (which is constituted in this case by the center 76 of the hemispherical ball 70 which coincides with the center of the hemispherical cap 72) into coincidence with the target point 12 which is defined in this case by the second focus of the truncated elliptical reflector 10.

The length of the second link element 26 is then adjusted so that the end 14a of the arm 14 is located at a predetermined distance D from the target point 12, thereby calibrating the distance between the free end 14a of the locating arm 14 and the device for triggering and focusing shots, and more precisely between said free end 14a of the arm and the target point 12.

This predetermined distance D is preferably not less than the greatest detection depth of the locating probe used, which probe will subsequently be mounted on the free end 14a of the arm 14. It will be understood that in order to adjust the length of the second link element 26 mounted on the free end 14a of the arm 14, it is easy to act on the nuts 46, 48, and 50.

It can thus be understood that the coordination means 20 comprising the link member 22 make it possible to coordinate the initial positions in three dimensions of the device 10 for triggering and focusing shots, and of the locating arm 14. The coordinates of this initial position of the locating arm are noted and are subsequently used for determining the position in three dimensions of the target to be destroyed, for example a lithiasis, by the position occupied by the locating arm in three dimensions at said moment, thereby making it possible to modify the position in three dimensions of the device 10 for triggering and focusing shots in order to bring the target point 12 into coincidence with the target to be destroyed.

It will thus be understood that the invention provides a method and apparatus for coordinating initial positions in three dimensions which are extremely simple, which are very easy to manipulate, and which make extremely accurate calibration possible. Further, and this constitutes a particularly advantageous feature of the invention, with the link member 22 mounted as shown in FIG. 1, and once the above-described calibration has been performed, the device 10 for firing and concentrating shots is moved successively along the three axes X, Y, and Z by predetermined distances with the locating arm being moved by the link member 22, and the new coordinates in three dimensions of the free end 14a of the arm 14 are detected.

This makes it possible to detect imperfections in the displacements in three dimensions of the device 10 for triggering and focusing shots and/or of the locating arm 14.

If the observed coordinates for the free end 14a of the arm 14 are different than the coordinates expected as a function of the predetermined displacement of the device 10 for triggering and focusing shots, then there is an imperfection in the displacement in three dimensions either of the device 10 for firing and concentrating shots, or else in the locating arm 14, or else in both of them.

These imperfections can then be corrected, and may be due to mechanical imperfections in the support for the device 10 for triggering and focusing shots or in the support of the locating arm 14.

Thus, the invention also makes it possible, in an unexpected manner, to correct for manufacturing imperfections either in the locating arm 14 or else in the support of the device 10 for triggering and focusing shots.

Naturally, the invention comprises any means which are technical equivalents to the means described and various combinations thereof, and it will be understood that any type of device 10 for triggering and focusing shots on a target point 12 may be used as may any type of locating arm capable of being displaced to any position in three dimensions.

We claim:

1. A method of coordinating the initial "reference" position in three dimensions of a device for triggering and focusing shots on a target point with the initial "reference" position of a locating arm, comprising the steps of:

providing a device for triggering and focusing shots on a target point;

providing a locating arm having a free end for supporting a removable locating probe, said probe replaceable by calibration means, for locating the position in three dimensions of a target whereupon the target point of the device for triggering and focusing shots may be brought into coincidence with the target;

adjusting the distance between the free end of the locating arm and the device for triggering and focusing shots by said calibration means to a "reference" distance value;

setting, in three dimensions, the position of the device for triggering and focusing shots and of the locating arm, when adjusted by the calibration means, as the initial "reference" position, in three dimensions, of the device for triggering and focusing shots and of the locating arm, respectively;

using said initial "reference" position for subsequently bringing the target point of the device for triggering and focusing shots into coincidence with the target from knowledge of a given position of the free end of the locating arm as determined by said "reference" distance value.

2. A method according to claim 1, wherein the distance which is calibrated is the distance between the free end of the arm and the target point.

3. A method of coordinating the initial "reference" position in three dimensions of a device for triggering and focusing shots on a target point with the initial "reference" position of a locating arm, comprising the steps of:

providing a device for triggering and focusing shots on a target point;

providing a locating arm having a free end for supporting a removable locating probe mounted for locating the position in three dimensions of a target whereupon the target point of the device for triggering and focusing shots may be brought into coincidence with the target; and coordinating the distance between the free end of the arm and the device for triggering and focusing shots, and moving the device for triggering and focusing shots successively along three axes X, Y and Z through predetermined distances in order to detect imperfections in the displacements in three dimensions of the locating arm and/or of the device for triggering and focusing shots.

4. A method of coordinating the initial "reference" position in three dimensions of a device for triggering and focusing shots on a target point with the initial "reference" position of a locating arm, comprising:

providing a device for triggering and focusing shots on a target point;

providing a locating arm having a free end for supporting a removable locating probe mounted for locating the position in three dimensions of a target whereupon the target point of the device for triggering and focusing shots may be brought into coincidence with the target;

providing a link member having a first end and a second end, said first end being removably securable to the device for triggering and focusing shots and the second end being removably securable on the free end of the locating arm when the probe is removed for coordination purpose;

coordinating the distance between the free end of the arm and the device for triggering and focusing shots by removably securing the link member between the free end of the arm and the device for triggering and focusing shots and by setting the position in three dimensions of the device for triggering and focusing shots and of the locating arm when coordinated by the link member as the initial "reference" position in three dimensions respectively of the device for triggering and focusing shots and of the locating arm.

5. A method according to claim 4, comprising moving the device for triggering and focusing shots successively along the three axes X, Y and Z by predetermined distances with the locating arm being moved by the link member, noting the new coordinates in three dimensions of the free end of the locating arm and when the observed new coordinates for the free end of the arm are different from the coordinates expected from the predetermined displacement of the device for triggering and focusing shots, correcting permanently the coordinates observed with the free end of the locating arm as a result of displacement of the device for triggering and focusing shots.

6. A method according to claim 4, wherein the step of providing a link member comprises providing a link member having a first and second link elements which are hinged to each other about a hinge which allows for displacement of the device of triggering and focusing shots and the locating arm in any of three dimensions, with the first link element being mounted on the device for triggering and focusing shots and with the second link element being mounted on the free end of the locating arm instead of and in the position of the locating probe.

7. A method according to claim 6, wherein said step of providing first and second link elements comprises providing link elements of adjustable length, wherein said coordinating step comprises causing the hinge point or axis between the link elements to coincide with the target point by adjusting the length of the link element which is mounted on the device for triggering and focusing shots, and wherein the distance between the free end of the arm and the target point is subsequently adjusted to a reference distance value by adjusting the length of the link element mounted on the arm.

8. A method according to claim 7, wherein said reference distance is not less than the greatest detection depth of the locating probe.

9. Apparatus for coordinating the initial "reference" position in three dimensions of a device for triggering and focusing shots on a target point with the initial "reference" position of a locating arm, comprising:

a device for triggering and focusing shots on a target point;

a locating arm supporting a locating probe on its free end for locating the position in three dimensions of a target, whereupon the target point of the device for triggering and focusing shots may be brought into coincidence with the target;

displaceable calibration means for adjusting the distance between the free end of the locating arm and the device for triggering and focusing shots to a "reference" distance value;

setting means for setting, in three dimensions, the position of the device for triggering and focusing shots and of the locating arm, when coordinated by the calibration means, as the initial "reference" position, in three dimensions, of the device for triggering and focusing shots and of the locating arm, respectively;

means for using said initial "reference" position for subsequently bringing the target point of the device for triggering and focusing shots into coincidence with the target from knowledge of a given position of the free end of the locating arm as determined by said "reference" distance.

10. Apparatus according to claim 9, wherein said distance comprises the distance between the free end of the arm and the target point.

11. Apparatus according to claim 9, wherein the device for triggering and focusing shots is constituted by a truncated ellipsoidal reflector.

12. Apparatus for coordinating the initial "reference" position in three dimensions of a device for triggering and focusing shots on a target point with the initial "reference" position of a locating arm, comprising: a device for triggering and focusing shots on a target point; a locating arm supporting a removable locating probe on its free end for locating the position in three dimensions of a target whereupon the target point of the device for triggering and focusing shots may be brought into coincidence with the target; and coordination means comprising a link member having a first end and a second end, said first end being removably securable to the device for triggering and focusing shots and the second end being removably securable to the free end of the locating arm when the probe is removed for coordination purposes, whereby the initial "reference" position in three dimensions of the device for triggering and focusing shots and of the locating arm may be set and the coordinates respectively of the initial "reference" position of the device for triggering and focusing shots and of the locating arm may be noted.

13. Apparatus according to claim 12, wherein the link member comprises a first link element and a second link element which are hinged to each other about a hinge which allows displacement in three dimensions of the device for triggering and focusing shots and the locating arm, wherein the first link element is mounted on the device for triggering and focusing shots, and wherein the second link element is mounted on the free end of the locating arm instead of and in the position of the locating probe.

14. Apparatus according to claim 13, wherein each link element is adjustable in length.

15. The apparatus of claim 13, wherein the hinge coincides with the target point.

* * * * *